United States Patent [19]

Ohtsuka et al.

[11] Patent Number: 5,266,248

[45] Date of Patent: Nov. 30, 1993

[54] METHOD OF PRODUCING HYDROXYLAPATITE BASE POROUS BEADS FILLER FOR AN ORGANISM

[76] Inventors: Torao Ohtsuka, 5-4-9 Fujiyama-dai, Kasugai-city, Aichi-prefecture; Makoto Fukaya, 2-515 Omoteyama, Tenpaku-ku, Nagoya-city, Aichi-prefecture; Hideo Tagai, 2-24-31 Denenchofu, Ohta-ku, Tokyo; Takayuri Kato, 125 Nishijima, Obata, Moriyama-ku, Nagoya-city, Aichi-prefecture; Shinpei Hashimoto, 4-40-2 Akasaka-cho, Chikusa-ku, Nagoya-city, Aichi-prefecture; Kazuhiko Sawai, Izumi-Sun heights 603, 1-7-5 Izumi, Hagashi-ku, Nagoya-city, Aichi-prefecture; Tomokazu Hattori, No. 2-No. 302 Lionsmanshion Fujigaokagarden 25 Aza, Higashi-harayama Ohaza Nagakute, Nagakutecho, Aichi-gun, Aichi-prefecture; Shigeo Niwa, 3-22 Kawasumi-cho, Mizuho-ku, Nagoya-city, Aichi-prefecture, all of Japan

[21] Appl. No.: 960,578

[22] Filed: Oct. 13, 1992

Related U.S. Application Data

[60] Continuation of Ser. No. 820,504, Jan. 14, 1992, abandoned, which is a division of Ser. No. 696,568, May 8, 1991, abandoned.

[51] Int. Cl.$^5$ .......... A01N 1/02; A61F 2/28; A61K 9/16; B05D 7/22
[52] U.S. Cl. ............ 264/44; 264/102; 264/129; 264/273; 264/279; 264/297.9; 424/423; 424/489; 424/500; 424/501; 427/2; 427/220; 427/238; 427/294; 523/115; 523/116; 623/16
[58] Field of Search ............ 264/42, 44, 59, 301, 264/62, 63, 65, 115, 117, 118, 122, 129, 101, 102, 273, 279, 297.9; 427/2, 215, 220, 238, 294; 424/489, 500, 501, 422, 423; 623/16; 523/113, 115, 116

[56] References Cited

U.S. PATENT DOCUMENTS

| | | | |
|---|---|---|---|
| 4,371,484 | 2/1983 | Inukai et al. | 264/81 X |
| 4,373,217 | 2/1983 | Draenert | 623/16 |
| 4,416,921 | 11/1983 | Dunn | 427/294 X |
| 4,547,390 | 10/1985 | Ashman et al. | 427/2 |
| 4,620,991 | 11/1986 | Young | 427/294 |
| 4,654,314 | 3/1987 | Takagi et al. | 264/44 X |
| 4,693,986 | 9/1987 | Vit et al. | 264/117 X |
| 4,737,411 | 4/1988 | Graves, Jr. et al. | 427/215 X |
| 4,749,585 | 6/1988 | Greco et al. | 427/2 |
| 4,839,215 | 6/1989 | Starling et al. | 623/16 X |
| 4,889,833 | 12/1989 | Nakamura et al. | 264/59 X |
| 5,030,396 | 7/1991 | Saita et al. | 264/44 |
| 5,032,445 | 7/1991 | Scantlebury et al. | 604/890.1 X |
| 5,034,352 | 7/1991 | Vit et al. | 264/117 X |

FOREIGN PATENT DOCUMENTS

| | | |
|---|---|---|
| 3531144 | 3/1986 | Fed. Rep. of Germany . |
| 174569 | 3/1983 | Japan ............ 264/59 |

*Primary Examiner*—Karen Aftergut
*Attorney, Agent, or Firm*—Rosen, Dainow & Jacobs

[57] ABSTRACT

A method of producing a hydroxylapatite base porous beads filler for an organism, including mixing hydroxylapatite powder having particle sizes not larger than 125 μm, in an amount ranging from 40 to 90% by weight, synthetic resin powder having particle sizes not larger than 74 μm, in an amount ranging from 5 to 55% by weight, and resinous binder in an amount ranging from 0.5 to 5% by weight to obtain a mixture, granulating the mixture to form beads each having a diameter ranging from 0.03 to 25 mm, firing the beads at a temperature ranging from 900° C. to 1180° C. to form hydroxylapatite base porous beads, dipping the porous beads in a colloidal solution, removing air from the porous beads under vacuum, and filling the colloidal solution into the pores in the porous beads under pressure.

7 Claims, 3 Drawing Sheets

1mm

METHOD OF PRODUCING HYDROXYLAPATITE BASE POROUS BEADS FILLER FOR AN ORGANISM

This application is a continuation of application Ser. No. 07/820,504, filed Jan. 14, 1992, now abandoned, which is a division of application Ser. No. 07/696,568, filed May 8, 1991, now abandoned.

BACKGROUND OF THE INVENTION

1. Field of the Invention

This invention relates to a hydroxylapatite base porous filler for an organism and a method of producing the same, which porous filler is suitable to be filled to an injured or diseased part (having a large bone loss) of the bone tissue for the purpose of achieving an early cure to promote rebirth of bone.

2. Description of the Prior Art

Hitherto, in case a bone of a human or an animal is partially cut out for the reason of an injury due to a traffic accident or the like and of a tumor or infection disease, an apatite block having a biocompatibility with a natural bone has been extensively used for curing a lost part. In this case, the apatite block inserted in a body for curing is usually joined with the natural bone. In the treatment of the bones and joints infections, especially clonic osteomyelitis, dosage of a pharmaceutical has been carried out under oral administration and/or injection in order to prevent a suppuration of a part of body subjected to the surgery and to promote the cure of the same.

However, difficulties have been encountered in the above-discussed curing method for the bone. That is to say, dosage of the pharmaceutical raises the concentration of the pharmaceutical uniformly throughout the whole organism body, so that a healthy part other than the injured or diseased part is also exposed to the pharmaceuticals thereby causing a possibility of making a side effect. Thus, it is difficult to raise a local concentration of the pharmaceuticals only at the injured or diseased part. Additionally, the pharmaceutical uniformly distributed throughout the whole organism body is decomposed and excreted under the action of various internal organs, and therefore the pharmaceutical concentration at the injured or diseased part is rapidly lowered.

In this regard, it has been proposed to use a means for gradually releasing the pharmaceutical. An example of such a proposition is disclosed in Japanese transactions of "Central Japan Orthopedics Disaster Science Society" Vol. 31, No. 5, annex, Pages 1882 to 1885, issued in 1988. In this proposition, bone cement beads formed of polymethylmethacrylate containing 3-4-dideoxykanamycin B is filled in the bone marrow at an injured or diseased part.

Further, mixing a variety of antibiotic materials with the synthetic resin-made cement beads is disclosed in Japanese transactions of "Central Japan Orthopedics Disaster Science Society" Vol. 32, No. 3, annex, Pages 1035 to 1040, issued in 1989.

Furthermore, Japanese transactions "Joint Surgery" Vol. 8, No. 12, Pages 65 to 71, issued in 1989 discloses the following: Synthesized hydroxylapatite fired at 900° C. is transplanted to a bone lost part in view of the fact that the main component of an animal's bone is hydroxylapatite. This transactions also shows that the transplanted synthesized hydroxylapatite is high in biocompatibility with a natural bone in an animal's body and exhibits an excellent curing effect.

Moreover, a Japanese technical magazine "Biomaterials" Vol. 8, No. 1, Pages 11 to 22 discloses the fact that hydroxylapatite which has been prepared by a wet synthesis was transplanted to a matured rabbit. The magazine also shows that transplanted hydroxylapatite exhibited an excellent biocompatibility with an organism bone, that formation of a new bone in direct contact with the synthesized hydroxylapatite was recognized, and that the compression strength of the bone at the implanted part increased until a time of several weeks after the implantation.

Of the above-discussed conventional techniques, one using the apatite block has a problem that growth of a new bone is slow at a joint part of the apatite block and the natural bone in the organism body after a surgery and treatment. One in which the apatite block and the natural bone are joined with each other by means of the metal piece has a problem of requiring removing the metal piece by carrying out a further surgery.

Additionally, the conventional synthesized hydroxylapatite can be formed porous as same as an organism bone in accordance with firing conditions. However, the conventional synthesized hydroxylapatite has a considerably fine and minute structure from a view point of absorbing and expelling the pharmaceutical, and therefore it is considerably low in porosity and has a low absorption amount of the pharmaceutical.

One in which the pharmaceutical is contained in the synthetic resin-made cement beads is disadvantageous because the cement beads remain in the organism body even after a predetermined amount of the pharmaceutical has been gradually released, thereby affecting the focus. Additionally, the synthetic resin-made cement beads are insufficient in amount of the pharmaceutical kept therein and in a time period throughout which the pharmaceutical is gradually released.

SUMMARY OF THE INVENTION

An object of the present invention is to provide an improved hydroxylapatite base porous filler for an organism which filler overcomes the above problems encountered in filler materials of the conventional techniques.

Another object of the present invention is to provide an improved hydroxylapatite base porous filler for an organism which filler has an excellent biocompatibility with the organism without serving as foreign matters, and a high pharmaceutical keeping ability while securing a predetermined long time period throughout which the pharmaceutical is released to the focus directly.

An aspect of the present invention resides in a hydroxylapatite base porous filler for a focus. The porous filler is comprised of fired hydroxylapatite base beads each of which is formed with a plurality of pores. Each pore has a diameter ranging from 1 to 100 $\mu$m and a length larger than the diameter. Each bead has a porosity ranging from 10 to 50% and a diameter ranging from 0.02 to 20 mm.

Another aspect of the present invention resides in a method of producing a hydroxylapatite base porous filler for an organism. The method is comprised of the following steps in the sequence set forth: (1) A mixture is prepared by mixing hydroxylapatite powder having a particle size not larger than 125 $\mu$m, in an amount ranging from 40 to 90% by weight, synthetic resin powder having a particle size not larger than 74 $\mu$m, in amount ranging from 5 to 55% by weight, and resinous binder in an amount ranging from 0.5 to 5% by weight. (2) The mixture is granulated to obtain beads each having a diameter ranging from 0.03 to 25 mm. (3) The beads are fired at a temperature ranging from 900° to 1180° C. to form the fired hydroxylapatite base beads.

Accordingly, the hydroxylapatite base porous filler of the present invention is excellent in affinity with an organism tissue, particularly a natural bone, maintaining a large amount of a pharmaceutical while expelling the maintained pharmaceutical throughout a long period of time as compared with similar recently developed conventional fillers. Additionally, the porous filler of the present invention does not make a side effect even when filled into an injured or diseased part inside the organism body, thus exhibiting excellent medical effects.

The hydroxylapatite base porous filler beads of the present invention are produced by the above-discussed method in which the hydroxylapatite powder having suitable particle sizes are mixed with the synthetic resin powder and then fired thereby forming many pores which reach the central part of each bead and are connected with each other. Such a manner for forming the pores seems to be unique in the art and makes possible to control the size of the pores during production, so that the hydroxylapatite base porous filler can maintain an optimum concentration of the pharmaceutical at the injured or diseased part throughout a long period of time while prolonging a pharmaceutical expelling time.

DETAILED DESCRIPTION OF THE INVENTION

Figure 1:
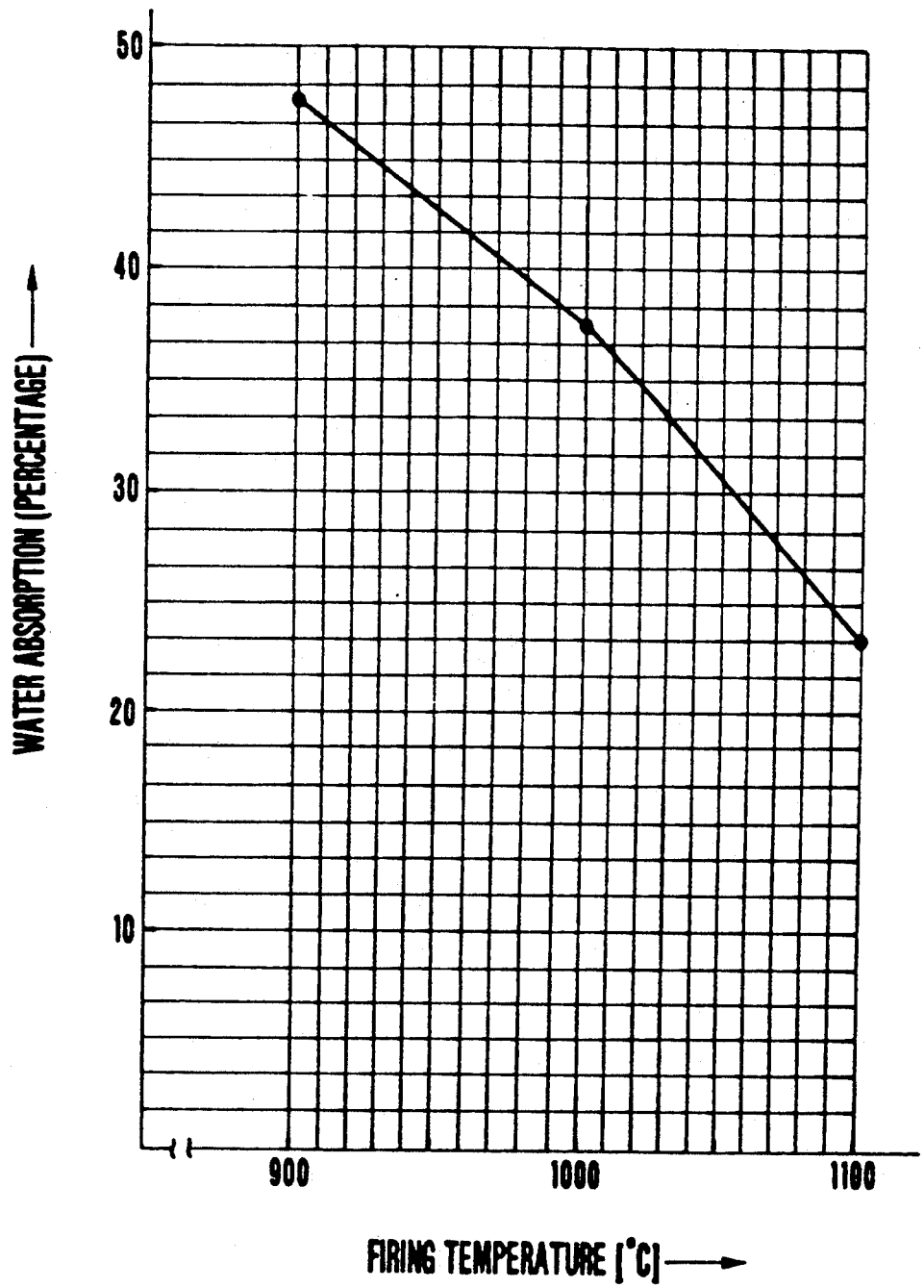
FIG. 1 is a graph showing the relationship between the water absorption percentage and the firing temperature in a fired hydroxylapatite base bead of the present invention.

According to the present invention, there is provided a hydroxylapatite base porous filler for an organism. The hydroxylapatite base porous filler comprises fired hydroxylapatite base beads each of which is formed with a plurality of pores. Each pore has a diameter ranging from 1 to 100 $\mu$m and a length larger than the diameter. Each bead has a porosity ranging from 10 to 50% and a diameter ranging from 0.02 to 20 mm. A part or whole of the pores may be filled with liquid or colloidal solution which may contain a pharmaceutical. It will be understood that each of the fired hydroxylapatite base beads is usually generally spherical but may not be generally spherical. In case that each fired hydroxylapatite base bead is not generally spherical, the "diameter" of the bead represents an average of the lengths of the minor and major axes of the bead. In this connection, in case that the cross-sectional shape of each pore may not be generally circular, in which the "diameter" of the pore represents an average of the breadth and the length of the cross-section of the pore.

The hydroxylapatite base porous filler is produced by the following steps in the sequence set forth: (1) A mixture is prepared by mixing hydroxylapatite powder having a particle size not larger than 125 $\mu$m, in an amount ranging from 40 to 90% by weight, synthetic resin powder having a particle size not larger than 74 $\mu$m, in amount ranging from 5 to 55% by weight, and resinous binder in an amount ranging from 0.5 to 5% by weight. (2) The mixture is granulated to obtain beads each having a diameter ranging from 0.03 to 25mm. (3) The beads are fired at a temperature ranging from 900° to 1180° C. to form the fired hydroxylapatite base beads. The pores of the resultant fired beads may be filled with a liquid (particularly one containing a pharmaceutical) after air is removed from the pore under vacuum.

The hydroxylapatite base porous filler for an organism of the present invention will be discussed in detail hereinafter. The diameter of each of the fired hydroxylapatite base beads is determined to be within a range between 0.02 to 20 mm for the reasons set forth below. This range is generally determined in order to use the porous filler for medical treatment of bones of animals including a small-size animal such as a mouse and for a large-size animal such as an elephant Additionally, the lower limit (0.02 mm) is decided because it is difficult to form hydroxylapatite base fired beads having a diameter lower than it. The upper limit (20 mm) is decided because the hydroxylapatite base fired beads having such a large diameter is sufficient even for a larger animal. Selection of the hydroxylapatite base fired beads within the above-mentioned range is carried out by sieving.

The diameter of each pore in each hydroxylapatite base fired bead is determined to be within the range between 1 to 100 $\mu$m for the reasons set forth below. If the diameter is less than the lower limit (1 $\mu$m), it is difficult to fill liquid into the pores. If the diameter is larger than the upper limit (100 $\mu$m), a pharmaceutical or a medicine filled in a liquid state in the pores is unavoidably expelled within a relatively short period of time since the pore having a large diameter provides a smaller capillary tube friction against the liquid pharmaceutical, thus making impossible to maintain a gradually expelling effect of the liquid pharmaceutical. It will be understood that this gradually expelling effect is very important to maintain the action of the pharmaceutical for a time as long as possible.

The porosity of each fired hydroxylapatite base bead is determined to be within the range between 10 to 50% for the reasons set forth below. If the porosity is lower than the lower limit (10%), a sufficient amount of pharmaceutical or the like can not be retained in the bead. If it is higher than the upper limit (50%), a sufficient strength of the bead cannot be obtained.

Next, the method of producing the hydroxylapatite base porous filler for an organism will be discussed in detail hereinafter. This production method is envisaged to provide the hydroxylapatite base porous filler which is excellent in affinity with an organism such as a bone and has a sufficient porosity and the pores of a size suitable for gradually expelling the pharmaceutical from the pores. In this production method, the particle size of a raw material or hydroxylapatite powder is selected to be not large r than 125 $\mu$m upon taking account of a dimensional reduction of fired products or beads. Additionally, in order to obtain the porosity of 10 to 50% of the fired bead, the synthetic resin powder in an amount of 5 to 55% by weight is mixed with the hydroxylapatite powder in the amount of 40 to 90% by weight to prepare raw materials. In the raw materials, the resinous binder in the amount of 0.5 to 5% by weight is added. The thus prepared raw materials are granulated to obtain the beads each having the diameter of 0.03 to 25 mm. Then, the beads are fired at the temperature of 900° to 1180° C. This firing temperature range is determined for the reasons set forth below. If the firing temperature is lower than the 900° C., joining strength at contact points of contacting hydroxylapatite powder particles is unavoidably lowered so that there may occur breakage of many fired hydroxylapatite base beads under friction during filling the liquid pharmaceutical into the pores of the fired beads under pressure. If the firing temperature is higher than 1180° C., there is a possibility of blocking the pores or capillary tubes formed in each fired bead. This will reduce the porosity of each fired bead to a value lower than 10%, so that the amount of the liquid pharmaceutical kept in each fired bead decreases thereby to hardly provide a promoted bone treatment effect.

It is preferable that a synthetic resin for the synthetic resin powder used in this production method is burnable without becoming into a flowable state when heated. An example of such a synthetic resin is a thermosetting resin such as phenolic resin. The resinous binder used in the production method preferably contains a slight amount of a sodium content in order to improve cohesion characteristics of the hydroxylapatite powder particles and therefore granulation upon adherence of the powder particles. In this regard, an example of the binder is sodium methacrylate.

The diameter range of each pore in the fired particles is determined to be of 1 to 100 μm which is effective for filling liquid pharmaceutical into the pores and for gradually expelling the pharmaceutical from the pores. This range is slightly altered depending upon the size of a molecule of the pharmaceutical, the viscosity of the liquid medicine and the like. If the diameter of the pore is smaller than 1 μm, a considerably long time is required for filling the pharmaceutical into the pores. If the pore diameter is larger than 100 μm, a time in which the pharmaceutical is being expelled is shortened thereby sharply degrading the gradually expelling effect for the pharmaceutical. Additionally, the length (depth) or longitudinal dimension of each pore in the fired bead is set to be larger than the diameter of the pore for the reasons set forth below. If the length of each pore is not larger than the diameter of the same, the time for which the medicine is being expelled is shortened while making impossible to fill a sufficient amount of the medicine into the pore.

The porosity of each fired hydroxylapatite base bead is determined to be 10 to 50%. This porosity becomes larger as the amount of the synthetic resin powder mixed with the hydroxylapatite powder increases, and becomes smaller as the same amount decreases. Additionally, the porosity may be controlled in accordance with the firing temperature and the firing time to obtain a required porosity. Controlling the size (length and diameter) of the pore in the fired particle is accomplished by adjusting the particle size of the synthetic resin powder mixed with the hydroxylapatite powder, so that the size of the pore enlarges in case of using the coarse synthetic resin powder while minimizes in case of using the fine one.

Function and significant advantages of the hydroxylapatite base porous filler for an organism of the present invention will be discussed hereinafter.

The affinity of hydroxylapatite with a natural bone seems to depend on assimilation of the hydroxylapatite with the bone tissue in the organism. Such affinity with the natural bone is never found in the conventional synthetic resin-made cement beads which have been the most recently developed in the above-discussed various conventional techniques.

Each bead of the hydroxylapatite base porous filler of the present invention is formed with many pores which may be filled with pharmaceutical. Accordingly, in case that the pharmaceutical is an antibiotic substance, the antibiotic substance can be expelled little by little throughout a certain long period of time in which a complete cure is reached, preventing suppuration of the injured or diseased part and making other curing actions, thus promoting a total cure of the injured or diseased part of the organism. It will be noted that such an effect has never been found in the conventional apatite block proposed before the conventional synthetic resin-made cement beads.

It will be appreciated that such a filler as to be provided with both a high affinity with a natural bone and a high effect of gradually expelling the pharmaceutical has not existed hitherto in the art, and therefore the principle of the present invention is highly advanced over the prior art or conventional techniques.

The production method of the present invention is characterized in that the hydroxylapatite powder is mixed with the synthetic resin powder which is slightly finer than the hydroxylapatite powder to form the beads; and the beads are fired at 900° C. to 1180° C., thereby forming the generally spherical beads each of which is formed with fine and minute pores reaching the central part of the bead. It is to be noted that the major fine pores are connected with each other at the deep part near the center of the spherical bead. Accordingly, if the pores are filled with the pharmaceutical, a high retention ability for and a high effect of the pharmaceutical can be obtained. The filler of the present invention having such a feature is in fact new and therefore the most excellent in a variety of conventional fillers.

In order to demonstrate the effect and advantages of the hydroxylapatite base porous filler of the present invention, experiments were carried out as discussed hereinafter.

EXAMPLE 1

First, an example of the production method for the hydroxylapatite base porous filler according to the present invention will be explained.

Hydroxylapatite available on the market was pulverized to obtain powder having particle sizes smaller than −65 mesh (65 mesh-under) or 0.2 mm. Then, phenolic resin powder having the same particle sizes was mixed in an amount of 10% by weight with the hydroxylapatite powder. Further, 10% by weight of sodium methacrylate as a binder was added to the above mixture. Then, a sufficient mixing was made among the three components. The thus mixed three components were sufficiently kneaded upon being supplied with about 50% by weight of water, and thereafter formed into generally spherical beads each having a diameter of about 12 mm. The beads were then dried.

These beads were divided into four batches A, B, C and D which were put in an electric furnace. In the electric furnace, the beads were heated to evaporate the volatile contents in the resin and the binder, and subsequently heated at 300° C. to 400° C. to sufficiently burn carbon content. Thereafter, the batches A, B, C and D were fired for 3 hours respectively at 900° C., 1000° C., 1100° C. and 1180° C., and subsequently gradually cooled at room temperature, thus obtaining the four batches of fired beads having a diameter of about 10 mm.

The above-mentioned sodium methacrylate had an ash composition shown in Table 1 upon being burnt or fired.

TABLE 1

| Component | Content |
| --- | --- |
| $Na_2O$ | 41.80% |
| $K_2O$ | 280 ppm |
| $CaO$ | 210 ppm |
| $Fe_2O_3$ | 97 ppm |
| $MgO$ | 81 ppm |
| $Al_2O_3$ | 50 ppm |
| $ZnO$ | 27 ppm |

The porosity of the resultant fired beads of each batch was determined by removing air from the pores of each fired bead under vacuum and thereafter by measuring a weight increase of each bead upon being dipped in water, in which the specific gravity of water was 1. As a result, the porosities of the fired particles of the batches A, B, C and D were about 50%, about 36%, about 25% and about 12%, respectively.

In connection with the above test, the relationship between the firing temperature of the bead and water absorption percentage of the resultant bead having a diameter of about 10 mm was determined. The result is shown in FIG. 1 and demonstrates that the water absorption of the fired bead reduces as the firing temperature of the same becomes high.

Figure 2:
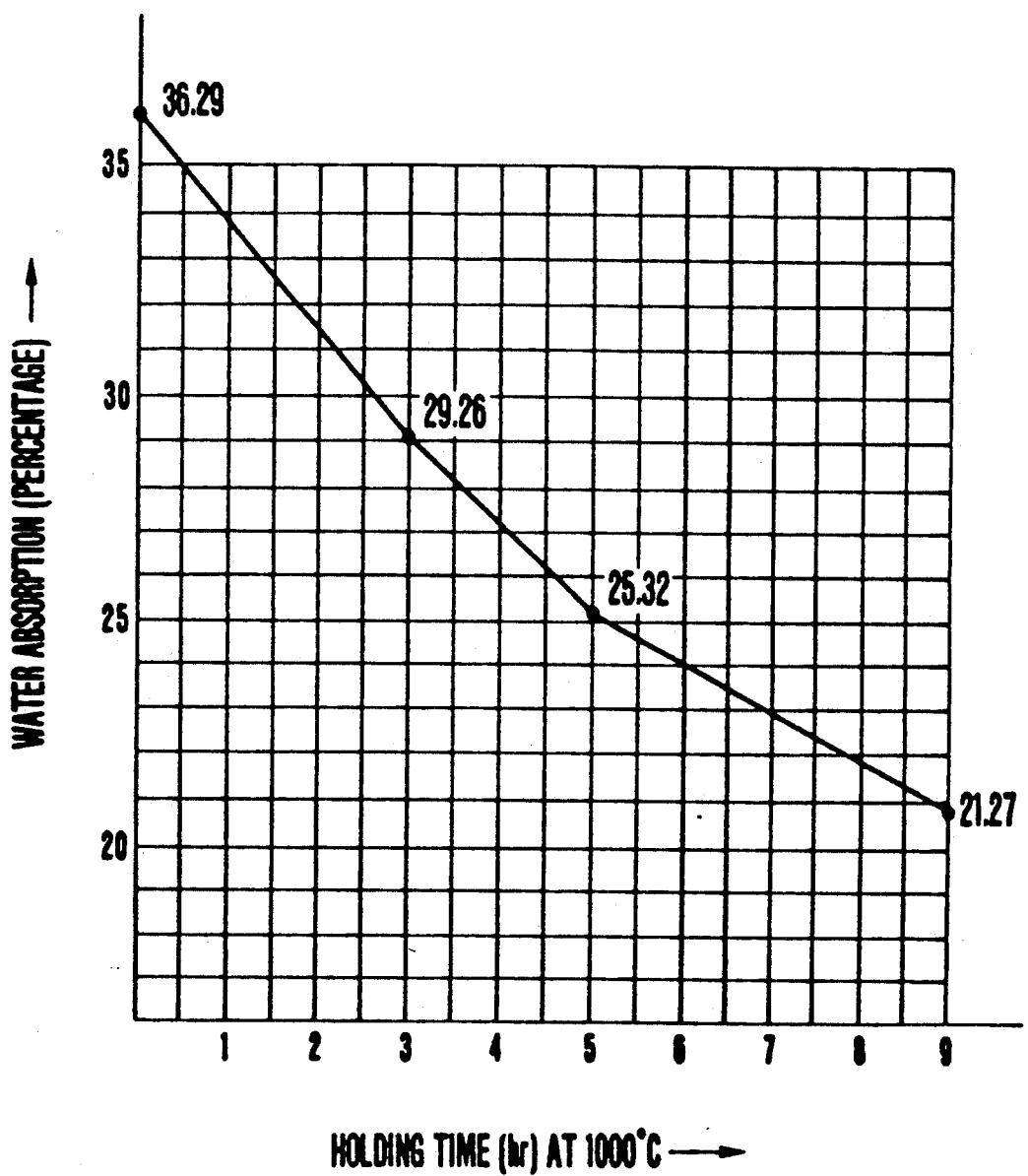
FIG. 2 is a graph showing the relationship between the water absorption percentage and the holding time at 1000° C. in firing.

Additionally, the relationship between the holding time (firing time) of the bead at 100° C. in the firing and the water absorption percentage of the resultant bead having a diameter of about 10 mm was determined. The result is shown in FIG. 2 and demonstrates that the water absorption of the resultant bead reduces as the firing time is prolonged.

The physical properties of the fired particles of the batches A, B, C and D were measured and are shown in Table 2.

TABLE 2

| | | Batch | | | |
| --- | --- | --- | --- | --- | --- |
| | | A | B | C | D |
| | | Temp. | | | |
| Item | Unit | 900° C. | 1000° C. | 1100° C. | 1180° C. |
| Water absorption percentage | % | 47.39 | 37.07 | 22.96 | 10.1 |
| Bulk density | $g/cm^3$ | 1.2493 | 1.4841 | 1.7814 | 1.8137 |
| Compression strength | Kgf | 3.0 | 5.6 | 8.0 | 8.0 |

As appreciated from the above, filling the pores of the fired hydroxylapatite base porous beads with water or pharmaceutical liquid is carried out as follows: First, the porous beads are dipped in the liquid (water or pharmaceutical liquid), upon which air is removed by putting a system including the beads and the liquid in a vacuum condition. After completion of air removal, the system is put in a pressurized condition under atmospheric pressure thereby filling the liquid into the pores of the beads.

EXAMPLE 2

This example concerns a case where hydroxylapatite base porous filler (fired beads) is applied to a material for pathology.

Figure 3:
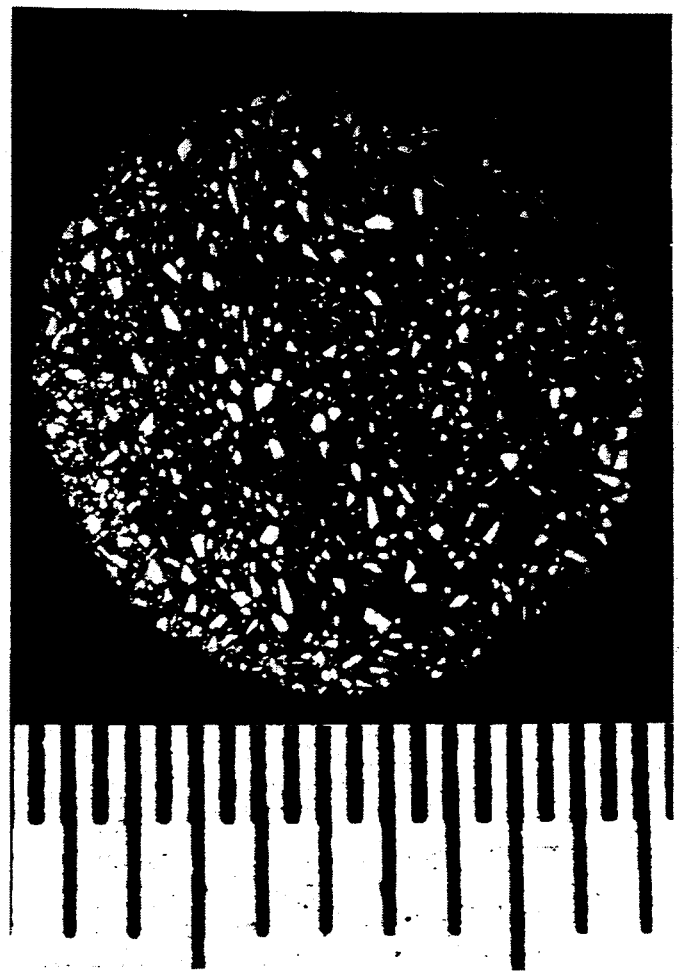
FIG. 3 is a micro-photograph showing a result of a test conducted on a hydroxylapatite base bead of the present invention.

First, a preliminary test was conducted, for example, by using a fired bead which had a diameter of about 10 mm and is shown in FIG. 3. In order to get the structure of each fired particle, the following test was first made: Red ink was injected into a pore of the fired bead, in which the red ink was oozed from the other many pores. This demonstrates that the major pores reached the central part of the fired bead and were connected with each other at the deep section near the center of the fired bead.

This pathological experiment was conducted as a part of a study of "Drug Delivery System (referred hereinafter to as DDS)" which had been made since several years before in order to attain a gradually releasing effect of antibiotic substance for the purpose of providing the antibiotic substance at a high concentration to the focus of the injured or diseased part, preventing suppuration and suppressing a side effect of the antibiotic substance.

The antibiotic substance used in this experiment was "3-4-dideoxykanamycin B (referred hereinafter and internationally to as DKB)". A test was conducted using DKB, in which a measurement was made to get the content of DKB filled into the pores of a fired filler bead having a diameter of about 5 mm and a weight of 0.097 g under a variety of degrees of vacuum (mmHg). The result is shown in Table 3 which depicts the relationship between the vacuum degree and the DKB content in the about 5 mm diameter bead. This result demonstrates that the content of DKB is the most in case the vacuum degree is 40 mmHg.

TABLE 3

| Vacuum degree (mm Hg) | 760 | 180 | 100 | 40 | 0 |
| --- | --- | --- | --- | --- | --- |
| DKB content (mg) per bead | 7.6 | 10.2 | 9.5 | 12.0 | 10.1 |

Additionally, another test was made by using DKB, in which a measurement was made to get the content of DKB filled into the pores of the fired filler bead having a diameter of about 5 mm and a weight of 0.097 g under a variety of the degree of vacuum and the concentrations (mg/ml) of the DKB solution. The result is shown in Table 4 which depicts the relationship between the DKB solution concentration and the DKB content in the 5 mm diameter bead. This result demonstrates that the content of DKB is generally proportional to the DKB solution concentration.

TABLE 4

| DKB solution concentration (mg/ml) | 125 | 250 | 375 | 500 |
| --- | --- | --- | --- | --- |
| DKB content (mg) per bead | 5.8 | 11.7 | 13.9 | 18.0 |

A further test was made by using three kinds of the hydroxylapatite base porous filler beads which were produced upon being fired respectively at 900° C., 1000° C. and 1100° C. The fired filler beads had a water absorption percentage ranging from 37.07% to 14.47% by weight. Each filler bead has a diameter of 5 mm. These filler beads were dipped in 250 $mg^B$/ml DKB solution. The system including the fired beads and the DKB solution was put under a vacuum of 40 mmHg to remove gas in the pores. Then, the system was put again under atmospheric pressure to fill the pores with the DKB solution. The filler beads filled with the DKB solution were subjected to a freeze drying to fix the DKB in the pores. Subsequently, a measurement was made to get the weight of the DKB filled in the pores of each filler bead. Additionally, a measurement was made to get the base or concentration of DKB which was eluted from the pores, in which the elution of DKB was carried out by dipping the freeze-dried filler bead in 1 ml of distilled water during a specific time. As a result, the weight of DKB filled in the pores was 80 mg (the most) per one bead in case of the filler bead whose firing temperature was 1000° C. and water absorption percentage was 37.07%, while the same weight was 35 mg (the least) in case of the filler bead whose firing temperature was 1100° C. and water absorption percentage was 14.47%. Finally, the concentration of DKB eluted in 1 ml of distilled water from the pores was a value ranging from 20 to 50 mg/ml which was about two times of that in the conventional bone cement bead having the same diameter as that of the filler bead used in this experiment. It will be appreciated from the above that the water absorption percentage is one of the factors for controlling the weight of DKB filled in the pores of the filler bead.

It is to be noted that even the conventional most recently developed synthetic resin-made bone cement beads contain an antibiotic substance only at its surface layer, so that the elution of the antibiotic substance is made only from the surface layer. Accordingly, an elution amount of the antibiotic substance is smaller thereby making impossible to maintain a sufficient concentration of the antibiotic substance at the focus of the injured or diseased part. However, in case of the filler beads of the present invention, it was revealed that the antibiotic substance could be filled into the central part of the filler bead, so that the content of the antibiotic substance filled in the filler bead was about two times that in the conventional bone cement bead, and the elution amount of the antibiotic substance was about four times that in the bone cement bead.

Furthermore, the conventional synthetic resin-made bone cement bead serves as a foreign matter for an organism, and therefore it is required to be replaced with an apatite block bone under a further surgery. However, according to the filler beads of the present invention, the filler beads are formed of hydroxylapatite which has a biocompatibility with an organism, and therefore no further surgery is necessary. As a result, using the filler beads of the present invention facilitates an early cure of an injured or diseased part which will be difficult to be cured by the conventional bone cement beads.

What is claimed is:

1. A method of producing a bone-replacement filler for an organism, comprising the following steps:
   mixing hydroxylapatite powder having particle sizes not larger than 125 μm, in an amount ranging from 40 to 90% by weight, synthetic resin powder having particle sizes not larger than 74 μm, in an amount ranging from 5 to 55% by weight, and resinous binder in an amount ranging from 0.5 to 5% by weight to obtain a mixture;
   granulating said mixture to form beads each having a diameter ranging from 0.03 to 25 mm;
   firing said beads at a temperature ranging from 900° C. to 1180° C. to form hydroxylapatite base porous beads having pores;
   dipping said porous beads in a colloidal solution;
   removing air from said porous beads under vacuum; and
   filling said colloidal solution into said pores in said porous beads under pressure to form said bone-replacement filler for an organism.

2. A method as claimed in claim 1, wherein said colloidal solution includes water and a pharmaceutical.

3. A method as claimed in claim 1, wherein said synthetic resin powder comprises thermosetting resin.

4. A method as claimed in claim 3, wherein said thermosetting resin is phenolic resin.

5. A method as claimed in claim 1, wherein said resinous binder contains sodium.

6. A method as claimed in claim 4, wherein said resinous binder is sodium methacrylate.

7. A method as claimed in claim 2, wherein said pharmaceutical includes an antibiotic substance.

* * * * *